United States Patent [19]

Finch, Jr.

[11] Patent Number: 4,517,972
[45] Date of Patent: May 21, 1985

[54] METHOD AND APPARATUS FOR APPLYING A THERAPEUTIC ARTICLE TO A BODY

[76] Inventor: Robert E. Finch, Jr., 326 N. Seventh St., Suite 204, Springfield, Ill. 62701

[21] Appl. No.: 457,249

[22] Filed: Jan. 11, 1983

[51] Int. Cl.³ .............................................. A61F 13/00
[52] U.S. Cl. ..................................... 128/156; 128/399
[58] Field of Search ............... 128/156, 157, DIG. 15, 128/163, 154, 171, 379, 380, 399, 402; 604/336, 337, 332, 342, 343, 344

[56] References Cited

U.S. PATENT DOCUMENTS

| | | | |
|---|---|---|---|
| 3,026,874 | 3/1962 | Stevens | 128/154 X |
| 4,205,678 | 6/1980 | Adair | 604/343 |
| 4,239,046 | 12/1980 | Ong | 128/DIG. 15 |
| 4,250,882 | 2/1981 | Adair | 128/154 |
| 4,263,906 | 4/1981 | Finley | 128/157 |

Primary Examiner—John D. Yasko
Attorney, Agent, or Firm—Berman, Aisenberg & Platt

[57] ABSTRACT

A method and apparatus for applying a therapeutic article to the body of a patient uses adhesive-backed strips which are applied around the injury, and the article is attached to the strips. The strips and the article preferably employ Velcro-type material, but may alternatively use magnetic substances, to removably secure the article to the patient. According to the method, the physician may determine the proper location of the article and apply the strips to hold the article there. The article may then be applied by a nurse or the patient.

5 Claims, 8 Drawing Figures

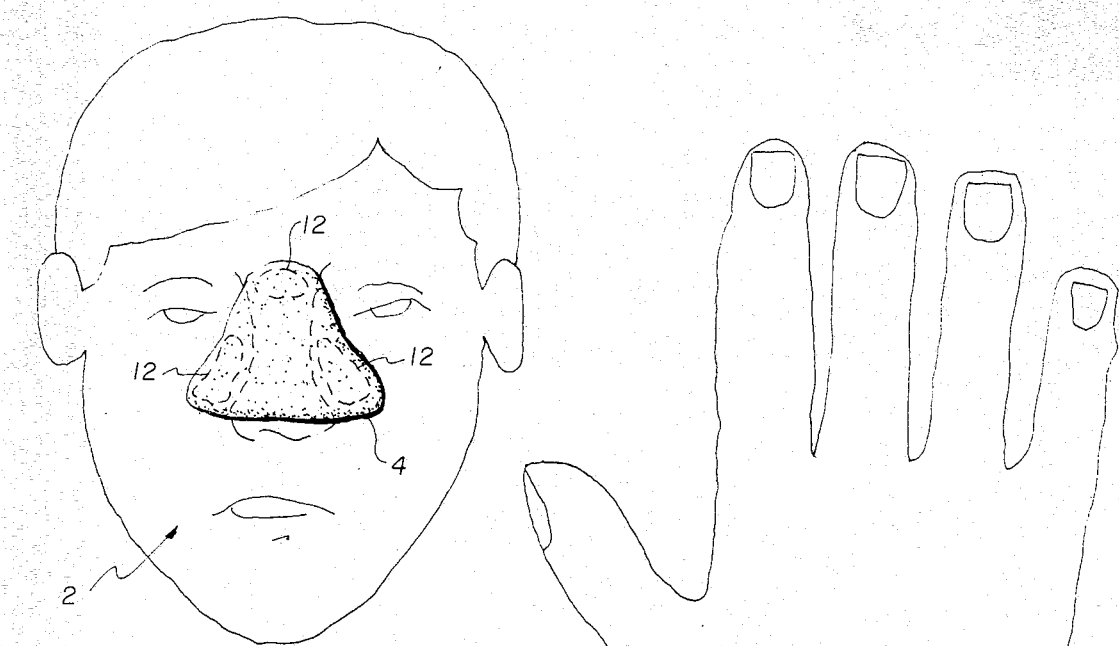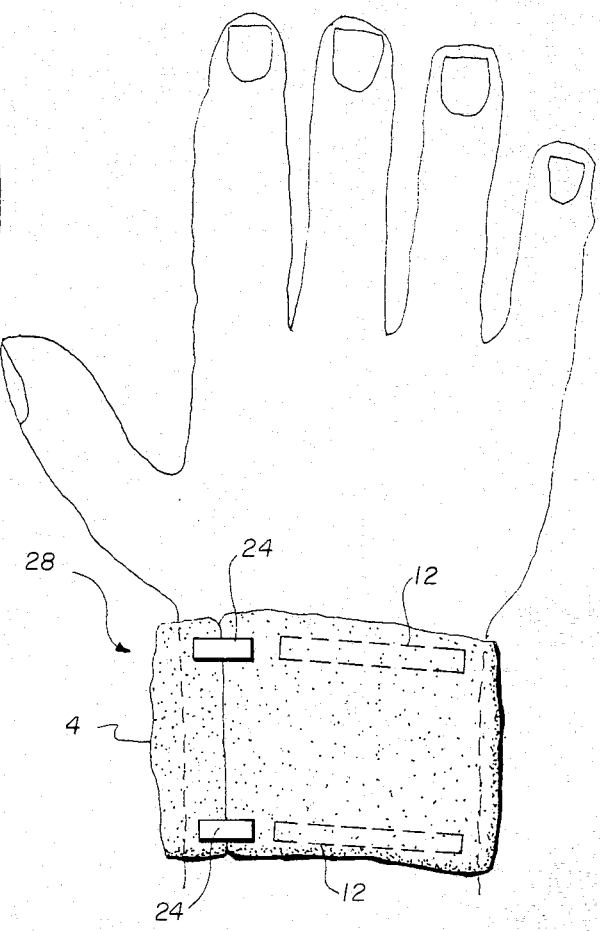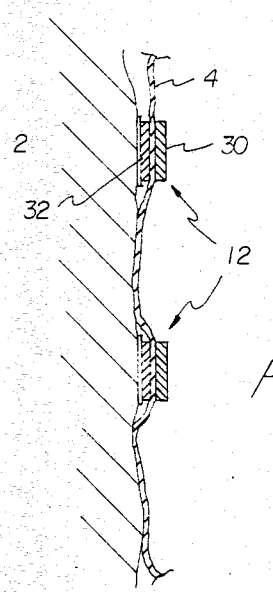

4,517,972

METHOD AND APPARATUS FOR APPLYING A THERAPEUTIC ARTICLE TO A BODY

TECHNICAL FIELD

This invention relates to the art of securing a therapeutic article to a human or animal body.

BACKGROUND ART

A known technique for treating a wide variety of physical ailments is to apply a therapeutic article, such as a hot or cold pack, to the affected area. A known hot pack is a common hot-water bottle, which is typically held on a desired part of the body by hand, or placed on a bed so that a patient may lie on top of it. Other hot packs, such as those which employ an exothermic chemical reaction as a source of heat, are common. Cold packs, such as ice wrapped in a towel, are similarly held to a bruised or injured area by hand. A cold pack may use an endothermic chemical reaction or may be refrigerated prior to its application to a patient.

It is often quite inconvenient for a patient to hold a therapeutic article on an affected area; this occupies the hands of the patient and thus limits the ability to perform other tasks or to move about.

U.S. Pat. Nos. 2,573,791 (Howells) and 3,952,735 (Wirtschafter et al.) teach therapeutic articles applied to the human body by the use of adhesive tabs. The patent to Howells teaches a bandage comprising a heated area surrounded by a flexible material having an adhesive backing. The adhesive serves to secure the entire article to the patient's body with the heated area overlying the injury. The article shown by Wirtschafter et al. also employs a bandage having a therapeutic portion surrounded by flexible material having an adhesive backing.

The articles described in these patents suffer from the disadvantage that they are not easily removable or replaceable. When these articles are removed from the patient's body, the adhesive material must also be removed. Thus, when applying an article, such as a hot pack, the patient is subjected to a continual removing and reapplying of an adhesive strip which is painful and also irritates the patient's skin.

It is also known to secure a therapeutic article to a patient's body by placing the article on the body and then wrapping a flexible strip or bandage around both the body part and the article. U.S. Pat. Nos. 4,036,220 (Bellasalma) and 3,815,610 (Winther) teach such a technique. The patent to Bellasalma teaches a water-proof covering which protects a bandage and is secured to a patient by a foam strip with ends which may be removably connected. Winther shows an envelope containing a hot pack which is placed around the neck of a patient, and a strip is then secured around the hot pack to hold it in place.

The technique of securing a therapeutic article to a patient with tape wrapped around the article and the body frequently results in excessive pressure being applied to the injury. Thus, the patient is forced to use his own hands to maintain the article in the proper position or to orient his body so that the article will naturally remain in the proper position.

SUMMARY OF THE INVENTION

The invention overcomes the above-mentioned disadvantages and facilitates the application of a therapeutic article to a patient by employing strips of material which have one surface adapted to be secured to a patient's body and a second surface adapted to be removably attached to the therapeutic article. The article has a surface which cooperates with the second surface of the strips to secure the article to the patient. The article and the second surface of the strips may employ a material, such as that sold under the trade name "Velcro", magnetic attraction, for example that created by a magnet sewn into the strips and a metal-containing material on the surface of the article, or other known attaching devices.

The invention includes determining the portion of the patient to be treated, placing the strips on the patient's body to provide means for attaching the therapeutic article, and placing the therapeutic article in contact with the attachment means. According to this method, the physician need not be involved with actually placing the article on the patient. Instead, the physician may merely place the strips in the appropriate locations, and a nurse or the patient may then place the therapeutic article on the patient's body in accordance with the location of the strips chosen by the physician.

The invention greatly facilitates regeneration of the therapeutic article, since it may be easily removed and replaced while the strips remain in position on the patient.

The method and apparatus of the invention allow a therapeutic article to be applied to a patient to avoid undue pressure, maintain patient mobility, permit easy regeneration of the article, and permit the patient to sleep without holding the article in position.

It is an object of this invention to provide a method for attaching a therapeutic article to a patient.

It is a further object of this invention to provide a method for removably attaching a thermal article, such as a hot pack or a cold pack, to an injured area of a patient.

It is another object of this invention to provide an apparatus for removably attaching a therapeutic article, such as a thermal pack, to the body of a patient.

BRIEF DESCRIPTION OF THE DRAWINGS

FIG. 5 is a front view of a therapeutic pack applied to a patient's nasal area in accordance with the invention.

FIG. 6 is a plan view of a therapeutic pack applied to a patient's wrist in accordance with the invention.

FIG. 7 is a partial cross section of a therapeutic pack applied in accordance with a second embodiment of the invention.

DETAILED DESCRIPTION OF THE INVENTION

Figure 1:
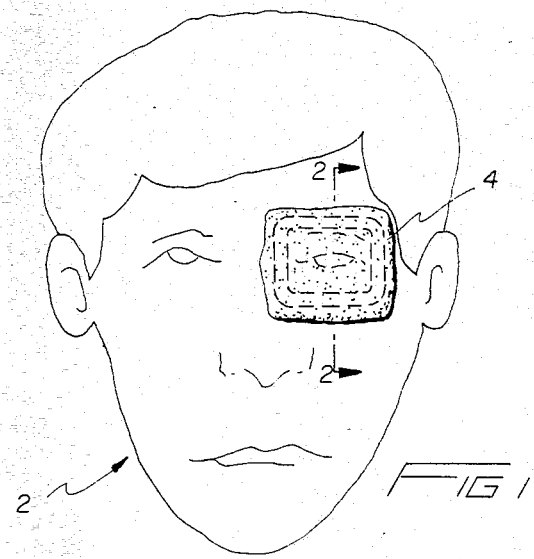
FIG. 1 shows the face of a patient, after ophthalmic surgery, having a therapeutic article applied in accordance with the invention.

FIG. 1 shows a patient 2 having an ocular injury such as an infection, or recovering from surgery. It is frequently desirable to treat such an injury with a therapeutic article 4, for example a hot pack or a cold pack, which may also contain an antiseptic.

Figure 2:
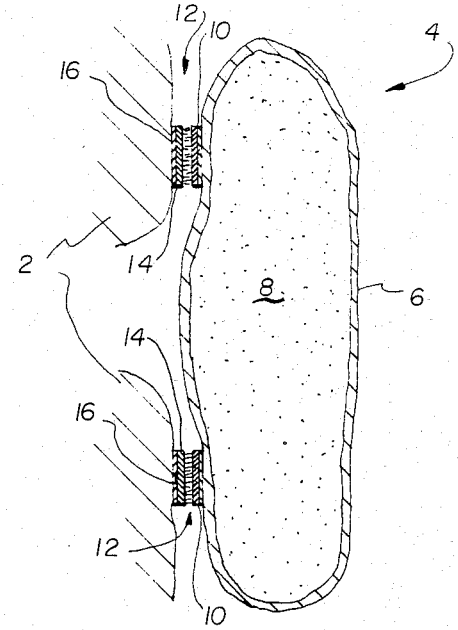
FIG. 2 is a cross section of the therapeutic article of FIG. 1 taken along line 2—2.

The therapeutic article 4 is easily attached to the patient's face using the principles of the invention shown more clearly in FIG. 2.

The therapeutic article 4 shown in FIG. 2 has an outer membrane 6 and an active region 8. The outer membrane 6 may be of a variety of materials, such as nylon, cotton, etc., and serves to contain the active components. The active region 8 may be hot water, ice, a chemical composition undergoing an exothermic or endothermic reaction, or an electrically heated pad.

A first portion 10 of an attachment means 12 is secured to the outer membrane 6 of the therapeutic article. A second portion 14 of the attachment means is secured to the patient. The second portion 14 preferably includes an adhesive 16 which secures the second portion to the patient's skin. The second portion 12 may, however, be secured to the patient's skin with other means.

The attachment means 12 shown in FIG. 2 is preferably of the type sold under the trademark "Velcro", and the first and second portions 10, 14 comprise hook and loop portions, respectively, which are secured together by pressing them into contact with each other. These portions are separated by simply pulling the second portion away from the first portion.

The separation between the patient's skin and the therapeutic article is somewhat exaggerated in FIG. 2 to allow adequate illustration of the attachment means 12. In practice the outer membrane 6 is essentially in contact with the patient's skin, for example, to transmit heat between the patient and the therapeutic article efficiently.

Figure 3A:
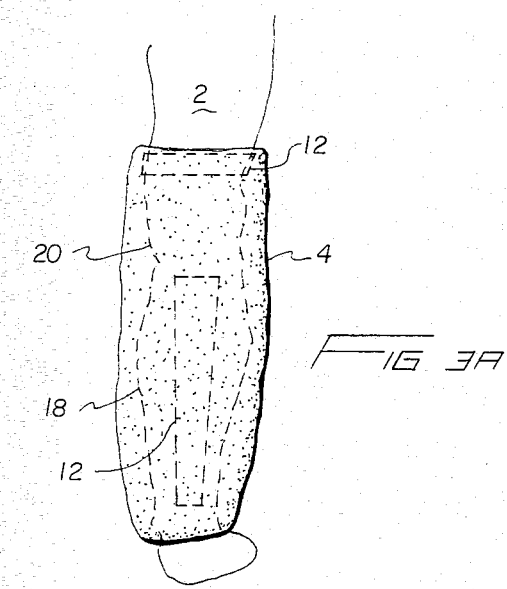
FIG. 3a is an end view of a therapeutic pack applied to a patient's calf and knee.

FIG. 3a shows the therapeutic article 4 attached to a patient's leg to cover the patient's calf 18 and knee 20. The attachment means 12 is applied at several discrete locations, such as down the back of the calf and around the lower portion of the thigh. This secures the therapeutic article to the patient in such a manner that he may move about or rest without fear of the article becoming displaced.

Figure 3B:
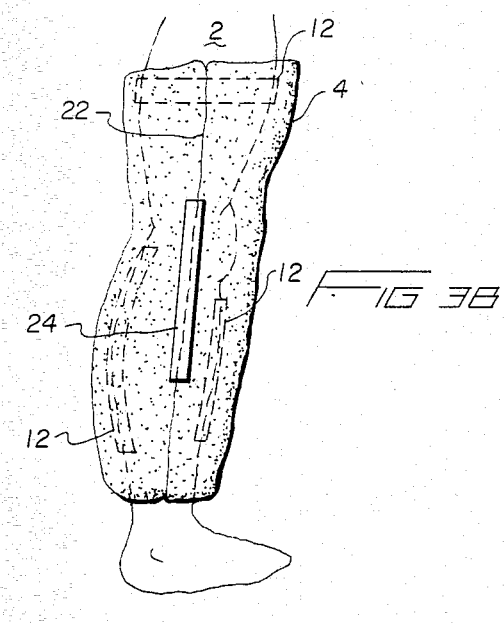
FIG. 3b is a side view of a therapeutic pack applied to a patient's calf, knee and thigh.

FIG. 3b shows how the therapeutic article 4 is wrapped around a patient's leg. A seam 22 formed by the abutting ends of the article may be covered with a piece of tape 24, such as adhesive tape or other fastening means. The article 4 is preferably designed for a particular portion of the body.

Figure 4:
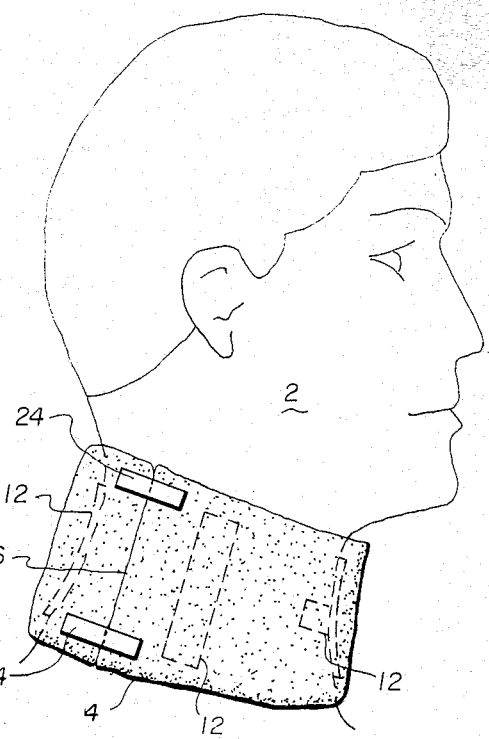
FIG. 4 is a side view of a therapeutic pack applied in accordance with the invention to the neck of a patient.

FIG. 4 shows an embodiment wherein the therapeutic article 4 has been applied to the neck of a patient 2. A plurality of attachment means 12 have been applied to the patient's neck to secure the therapeutic article effectively and directly to the patient's neck. The therapeutic article shown in FIG. 4 has a seam 26 secured by tapes 24 in a manner similar to that shown in FIG. 3b. It should be noted that these tapes may be entirely omitted, if desired, because the attachment means 12 will normally secure the therapeutic article to the patient.

FIG. 5 shows a therapeutic article 4 applied to the nasal area of a patient to treat an injury such as a nasal fracture. A plurality of attachment means 12 are spaced evenly around the patient's nose, and the therapeutic article is then conveniently secured to the attachment means.

FIG. 6 shows a therapeutic article 4 applied to the wrist 28 of a patient. A plurality of attachment means 12 may be applied to the patient's skin to secure the therapeutic article to the patient's wrist. Tape 24 is optionally used to secure the ends of the therapeutic article together.

FIG. 7 shows how the attachment means 12 may employ magnetic attraction to secure the therapeutic article 4 to a patient. The first portion of the attachment means 12 may be a magnetic material 30, such as a known ceramic magnet, and the second portion 32 may be a magnetic metallic tape having iron filings and an adhesive surface to secure it to the patient 2.

While the first portions of the attachment means shown in FIGS. 2 and 7 have been illustrated as discrete, spaced elements, it should be understood that they alternatively cover a large portion of the surface of the therapeutic article to obviate the necessity of aligning the first and second portions of the attachment means. For example, if the entire surface of the membrane 6 (shown in FIG. 2), which faces the patient, were covered with a Velcro material, it would not be necessary to align the first and second portions carefully to secure the therapeutic article to the patient.

In the method according to the invention, the physician first determines the optimum location of the therapeutic article, places the second portion of the attachment means around the location, and secures it to the patient. The article may then be applied by the physician, the patient or a nurse.

While the preferred embodiment has been described, other embodiments within the scope of the claims will be apparent.

It is claimed:

1. Apparatus for applying a thermal treatment to the body of an animal comprising
   (a) thermal treatment means for producing a temperature higher or lower than the skin temperature of said animal, and
   (b) attachment means for securing said article to said body comprising an elongate strip having adhesive thereon for securing said strip to said body and a second surface for cooperating with a surface of said thermal treatment means,
   (c) said surface of said thermal treatment means comprising removable attachment means for engaging said second surface to removably attach said thermal treatment means to said animal, said removable attachment means having a width substantially larger than the width of said elongate strip.

2. The apparatus of claim 1 wherein said second surface includes hook means for cooperating with loop means on said removable attachment means for removably securing said article to said strip.

3. The apparatus of claim 1 wherein said second surface includes loop means for cooperating with hook means on said removable attachment means for removably securing said article to said strip.

4. A method of securing a thermal treatment article to the body of an animal comprising
   (a) determining the desired site on said body for said article;
   (b) securing to said body adjacent said site a plurality of discrete means for attaching said article, each of said plurality having a first surface comprising adhesive means and a second surface comprising first removable attachment means,
   (c) attaching said article to said second surface of said means for attaching by engaging a second removable attachment means on said article with said first removable attachment means.

5. Apparatus for applying a thermal treatment to a body comprising securing means, and thermal treatment means, said securing means comprising a strip having a first surface covered with an adhesive and a second, opposed surface covered with a first portion of a removable attachment means, said thermal treatment means comprising a thermal mass having a temperature higher or lower than that of said body and a covering surrounding said thermal mass, said covering having a second portion of said removable attachment means thereon for cooperation with said first portion to secure said thermal treatment means to said body wherein said thermal mass has a bulk and weight similar to those of an ice pack or a hot water bottle.

* * * * *